United States Patent [19]

Pielkenrood

[11] 4,038,974

[45] Aug. 2, 1977

[54] APPARATUS FOR PRODUCING A GERM-FREE AIR FLOW IN THE VICINITY OF AN OPERATING TABLE

[75] Inventor: Simon Pielkenrood, Jaandijk, Netherlands

[73] Assignee: Pielkenrood-Vinitex B. V., Assendelft, Netherlands

[21] Appl. No.: 675,283

[22] Filed: Apr. 9, 1976

[30] Foreign Application Priority Data

Apr. 18, 1975 Netherlands ........................ 7504683

[51] Int. Cl.[2] ............................................ A61B 19/00

[52] U.S. Cl. ........................................ 128/1 R; 98/36

[58] Field of Search ................... 128/1 R, 132 R, 1 B; 98/36

[56] References Cited

U.S. PATENT DOCUMENTS

| | | | |
|---|---|---|---|
| 175,569 | 4/1876 | Lea | 98/36 |
| 2,593,702 | 4/1952 | Schneible | 98/36 |
| 3,505,989 | 4/1970 | Truhan | 128/1 R |
| 3,708,414 | 1/1973 | Laube | 98/36 |
| 3,820,536 | 6/1974 | Anspach et al. | 128/132 R |
| 3,859,993 | 1/1975 | Bitner | 128/132 R |
| 3,881,477 | 5/1975 | Von Otto | 128/132 R |

*Primary Examiner*—Lawrence W. Trapp
*Attorney, Agent, or Firm*—George F. Smyth

[57] ABSTRACT

An apparatus for producing a germ-free air flow in the vicinity of an operating table, comprising a coherent unit of a blower, filter means and air discharge pipes, which unit is to be positioned below an operating table in such a manner that the air discharge pipes extend below the lateral edges of the table, said pipes being provided with apertures adapted for directing air flows in a laterally downward direction.

10 Claims, 4 Drawing Figures

Figure 1:
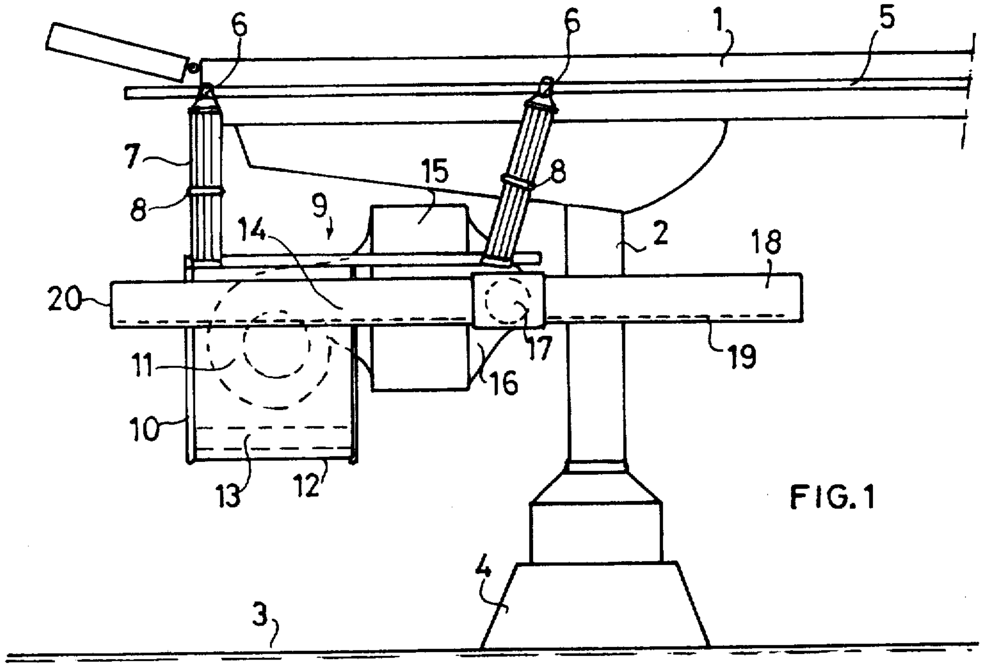

APPARATUS FOR PRODUCING A GERM-FREE AIR FLOW IN THE VICINITY OF AN OPERATING TABLE

In the prior U.S. Pat. No. 3,893,457 an operating table has been described which is provided with an air filter cabinet having a vertical exit surface for producing a horizontal germ-free air flow covering the space above the operating table as well as two spaces laterally of this table in which, during an operation, the surgeons and nurses are present, which lateral spaces are delimited by curtains extending downwards to a certain distance from the floor which is smaller than the height of the operating table. Moreover use is made of an auxiliary means, in particular two mutually parallel tubes, which are to be mounted below and along the lateral edges of the table and which are provided with air discharge openings. The latter openings are directed obliquely downwards so as to produce air flows which are directed towards the opening below the corresponding curtain, so as to prevent that dust that is possibly whirled up by the feet and legs of the persons present beside the table will reach the upper side of the operating table, and at the same time penetration of unfiltered air from below these curtains is counteracted. In particular these tubes can be supplied with cleaned air from the filter cabinet, but it is also possible to connect these tubes to a separate filter unit.

Such auxiliary means for producing a germ-free air flow are only required in those cases in which normal disinfection measures are insufficient. As a rule it is not justified to reserve an operating table in an operating theatre exclusively for such special cases. Thus the various parts such as the filter cabinet and the apertured tubes will, generally, be constructed as detachable units which can be connected at will to the operating table, and which, moreover, can be easily stored.

It is, however, often objectionable to include the air supply means for the afore-mentioned tubes in the main filter cabinet, whereas a separate control of the air flow through these tubes can be desirable. The use of a separate blower-filter unit to be connected to said tubes by means of air hoses is, however, objectionable during an operation as well.

The invention provides an apparatus of this kind which does not have these objections. To that end this apparatus comprises two parallel tubes to be arranged at or near the lower side of an operating table and provided with air discharge openings which are directed laterally downwards, which tubes are assembled with a blower and a filter box to a unit which is adapted to be positioned below an operating table.

Such a unit can, for instance, be suspended under an operating table by means of straps of variable length, or can be mounted on a movable under-carriage which can be positioned under an operating table. This assembly will not take up useful space then, and can be stored in a simple manner.

Figure 2:
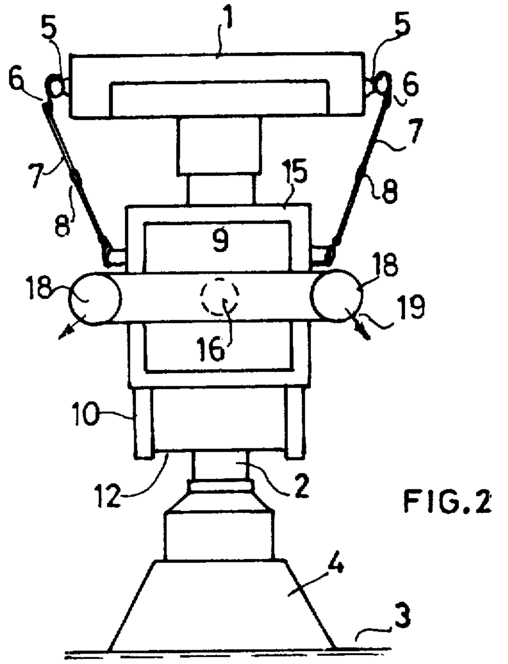
Figure 3:
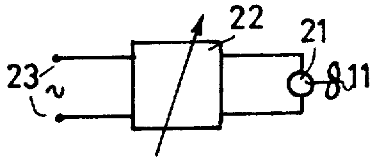

The invention will be elucidated below by reference to a drawing, showing in:

FIG. 1 a schematic lateral view of an apparatus according to the invention;

FIG. 2 a front view of this apparatus;

FIG. 3 a simplified circuit diagram of the blower of this apparatus, and

Figure 4:
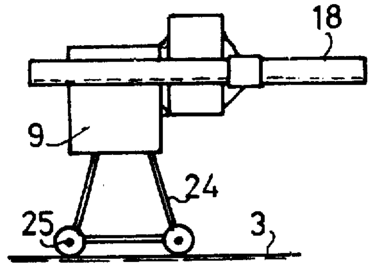

FIG. 4 a view at a smaller scale corresponding to FIG. 1 of another embodiment of this apparatus.

In the prior U.S. Pat. No. 3,893,457 devices have been described by means of which a germ-free air flow can be directed over an operating table and through the laterally adjacent spaces, which spaces can be delimited by curtains having a lower edge which is situated not substantially below the table surface, means being provided for directing laterally downward air flows into these spaces which can escape below these curtains.

In the drawing such an operating table 1 is schematically indicated, and the parts for generating an air flow over and along this table are not shown. This table is supported in the centre by a column 2 provided with a foot 4 resting on a floor 3.

This foot can comprise, for instance, wheels with blockings means if the operating table should be movable, but it can also be fixed to the floor. The column 2 is generally adjustable in height, and generally also the inclination of the table 1 in respect of this column will be variable.

At the lateral sides of the table 1 rods 5 are provided in the case shown. Hooks 6 of carrying straps 7 can be attached to these rods, which straps are provided with buckles 8 for changing the length thereof. These straps are, at their lower ends, connected to an air supply unit 9.

This unit 9 comprises a blower cabinet 10 within which a blower 11 is arranged, the suction end thereof communicating with the inner space of this cabinet. The cabinet 10 is, at its lower side, provided with an air suction opening 12, behind which a primary filter 13 is positioned for removing coarser dust from the air taken in. The blowing end 14 of the blower 11 communicates with a filter box 15 in which a fine dust filter is to be inserted which is able to provide the desired germ-free condition of the air. The other side 16 of this filter box communicates with a transverse tube 17, both ends of which connect to a corresponding longitudinal tube 18, which longitudinal tubes 18, when the whole assembly is suspended by means of the straps 7, extend parallel to the lateral sides of the operating table 1.

The tubes 18 are provided with a plurality of discharge openings 19 which are directed obliquely downwards so as to obtain obliquely downward air flows directed towards the opening below the curtains. As described in the prior patent application mentioned above, these air flows will counteract dust from being whirled up, and will, moreover, restrict the penetration of air from the environment below the curtains defining the space laterally of the operating table.

If desired both tubes 18 can be interconnected at the head end 20 by means of a transverse tube not shown, by means of which air flows directed obliquely downwards in the longitudinal direction of the table 1 can be produced as described in the above-mentioned prior patent application.

In order to obtain always a sufficiently strong air flow irrespective of the degree of soiling of the filters, it is advisable to design the blower 11 in such a manner that it is able to overcome the air resistance at the highest admissible degree of soiling of the filters. Since, then, the blower effect at a lesser soiling will be too strong, the rotational speed can be reduced accordingly. In FIG. 3 a preferred circuit arrangement is shown, in which the motor 21 of the blower 11 is connected to the mains 23 by means of a variable transformer 22 which is designed so that an adapted speed control of the motor 21 in the desired range can be obtained. The operation of this unit can be monitored by means of a manometer or the like, and the transformer is then to be adjusted as soon as the amount of air passed by the filters decreases. It will be clear that this transformer can also be adjusted automatically, and that instead of a variable transformer also another kind of current regulator can be used.

It is, furthermore, possible to mount the unit 9 in the manner shown in FIG. 4 on a under-carriage 24 provided with wheels 25, so that, then, the unit can be rolled below the operating table, which carriage should, of course, be constructed so that it remains free from the column 2 and the foot 4. In the case of an operating table adjustable in height, this carriage should be made adjustable as well. The advantage of the embodiment shown in FIG. 1 with suspension straps is that the unit will follow the height adjustment of the operating table automatically.

Within the scope of the invention many modifications are possible. For instance the suction opening 12 can be provided in the front wall or in one or more side walls of the cabinet 10, and it is also possible to provide a plurality of suction openings 12 which can be closed at will by means of a damper or the like so as to adapt the suction to the desired flow pattern. The primary filter 13 can also be arranged in the filter box 15 if desired.

I claim:

1. An apparatus, including a filter and a blower connected to the filter for driving air through it, to produce a substantially germ-free air flow in the vicinity of an operating table, and apparatus comprising:

two tubes, connected to the filter and having air discharge openings for producing a generally laterally downwardly directed flow of air, said two tubes extending generally parallel to the lateral edges of the operating table and located along with the filter and the blower beneath the operating table.

2. The apparatus of claim 1 futher comprising suspension means for suspending the filter and blower from the operating table.

3. The apparatus of claim 2 wherein said suspension means further comprises straps of adjustable length.

4. The apparatus of claim 1 further comprising a cart-like undercarriage on which the blower, the filter and said two tubes are carried, whereby the apparatus can be selectively positioned beneath and removed from beneath the operating table.

5. The apparatus of claim 1 wherein the blower and the filter are located between said two tubes.

6. The apparatus of claim 1 further comprising a laterally-extending manifold tube connecting the filter to said two tubes to distribute filtered air to said two tubes.

7. The apparatus of claim 6 wherein said laterally-extending manifold tube is attached to each of said two tubes substantially at their mid-points.

8. The apparatus of claim 6 wherein said laterally-extending manifold tube is attached to each of said two tubes at one end thereof to form a generally U-shaped tubular structure.

9. The apparatus of claim 6 wherein said laterally-extending manifold tube is provided with air discharge openings.

10. The apparatus of claim 1 wherein the blower is operable at more than one speed including a maximum speed adequate to cause a predetermined rate of air discharge even when the filter is soiled to a predetermined maximum extent.

* * * * *